(12) United States Patent  (10) Patent No.: US 9,005,728 B2
Johnston et al.  (45) Date of Patent: Apr. 14, 2015

(54) DISPOSABLE ABSORBENT PAD

(75) Inventors: Angela Ann Johnston, New London, WI (US); Jon Philip Rooyakkers, Appleton, WI (US); Joseph Daniel Coenen, Kaukauna, WI (US); Marcille Faye Ruman, Oshkosh, WI (US); Christopher Heiting, Black Creek, WI (US)

(73) Assignee: Kimberly-Clark Worldwide, Inc., Nennah, WI (US)

( * ) Notice: Subject to any disclaimer, the term of this patent is extended or adjusted under 35 U.S.C. 154(b) by 357 days.

(21) Appl. No.: 13/291,871

(22) Filed: Nov. 8, 2011

(65) Prior Publication Data
US 2013/0115437 A1  May 9, 2013

(51) Int. Cl.
| *B32B 9/00* | (2006.01) |
| *B32B 33/00* | (2006.01) |
| *A61F 13/15* | (2006.01) |
| *B32B 3/00* | (2006.01) |
| *A61F 5/48* | (2006.01) |
| *A61F 13/539* | (2006.01) |
| *B32B 7/12* | (2006.01) |
| *C09J 7/02* | (2006.01) |

(52) U.S. Cl.
CPC ............. *B32B 3/00* (2013.01); *C09J 7/0296* (2013.01); *A61F 5/485* (2013.01); *A61F 13/539* (2013.01); *A61F 2013/15056* (2013.01); *A61F 2013/53908* (2013.01); *B32B 7/12* (2013.01)

(58) Field of Classification Search
CPC ....... A61F 13/58; A61F 13/539; A61F 5/485; A61F 2013/53908; A61F 2013/15056; A61F 13/15; A61F 13/359; A47C 31/105; A47C 27/005; C09J 7/02; C09J 7/0296
USPC .............. 428/40.1, 41.8, 68, 343, 317.1, 198, 428/195.1, 137; 5/487, 482, 496, 498; 604/358, 391, 365, 389, 498
See application file for complete search history.

(56) References Cited

U.S. PATENT DOCUMENTS

| 239,193 A | 3/1881 | Rescinski |
| 1,916,640 A | 7/1933 | Rubin et al. |
| 2,414,927 A | 1/1947 | Chapman |
| 3,407,414 A | 10/1968 | Burns et al. |
| 3,576,039 A | 4/1971 | Roberts |
| 3,646,624 A | 3/1972 | Zipf, III |
| 3,654,059 A | 4/1972 | Zisblatt |
| 4,021,870 A | 5/1977 | Walters |
| 4,097,943 A | 7/1978 | O'Connell |

(Continued)

FOREIGN PATENT DOCUMENTS

WO  WO 2005108442 A1 * 11/2005

OTHER PUBLICATIONS

StaPut Flat Adhesive 30×36 inches, available at http://protectivebedding.com/staput-flat-adhesive-underpad-30×36-inches.html, printed Nov. 8, 2011, 2 pages.

(Continued)

*Primary Examiner* — Patricia L Nordmeyer
(74) *Attorney, Agent, or Firm* — Armstrong Teasdale LLP

(57) ABSTRACT

A disposable absorbent pad has an absorbent structure configured to absorb fluid. The disposable absorbent pad is adapted to provide a shear strength between the pad and the substrate when the pad is adhered to the substrate between about 1,500 grams per square inch and about 3,500 grams per square inch.

27 Claims, 14 Drawing Sheets

(56) References Cited

U.S. PATENT DOCUMENTS

| | | | |
|---|---|---|---|
| 4,166,464 A * | 9/1979 | Korpman | 604/366 |
| 4,549,323 A | 10/1985 | Brockhaus | |
| 4,572,174 A | 2/1986 | Eilender et al. | |
| 4,813,944 A | 3/1989 | Haney et al. | |
| 5,012,540 A | 5/1991 | Hockaday | |
| 5,099,532 A | 3/1992 | Thomas et al. | |
| 5,221,273 A | 6/1993 | Graham | |
| 5,433,715 A | 7/1995 | Tanzer et al. | |
| 5,486,167 A | 1/1996 | Dragoo | |
| 5,910,137 A * | 6/1999 | Clark et al. | 604/387 |
| 6,045,900 A * | 4/2000 | Haffner et al. | 428/315.9 |
| 6,187,696 B1 * | 2/2001 | Lim et al. | 442/77 |
| 6,675,702 B1 | 1/2004 | Maksimow | |
| 7,103,929 B2 | 9/2006 | Pilling et al. | |
| 7,836,533 B2 | 11/2010 | Rosenberg | |
| 2003/0121101 A1 * | 7/2003 | Corzani et al. | 5/487 |
| 2003/0124928 A1 | 7/2003 | Sherrod et al. | |
| 2004/0060112 A1 * | 4/2004 | Fell et al. | 5/484 |
| 2005/0234415 A1 * | 10/2005 | Liu | 604/361 |
| 2007/0056096 A1 | 3/2007 | Assink | |
| 2008/0107861 A1 * | 5/2008 | Dalal et al. | 428/99 |
| 2008/0132863 A1 | 6/2008 | Waksmundzki et al. | |
| 2008/0306462 A1 | 12/2008 | Bruckner et al. | |
| 2009/0004452 A1 | 1/2009 | Assink | |

OTHER PUBLICATIONS

Tranquility Incontinence Products . . . Peach Sheet Underpad, available at http://www.tranquilityproducts.com/dealers/products/maximum/peachsheet.htm, printed Nov. 8, 2011, 1 page.

International Search Report and Written Opinion for PCT/IB2012/055676 dated Mar. 20, 2013; 11 pages.

* cited by examiner

DISPOSABLE ABSORBENT PAD

FIELD

The field of this invention relates generally to disposable absorbent pads for absorbing fluids and more particularly to a disposable absorbent pad having adhesive for adhering the pad to a substrate.

BACKGROUND

Some individuals experience bedwetting during their sleep. This condition, which is known as nocturnal enuresis, can cause the affected individual emotional distress and adversely impact their self-esteem. One group of individuals with a higher potential for nocturnal enuresis is children approximately between the ages of four and twelve years old. Some of these children may no longer wear diapers or other types of absorbent garments but continue to experience bedwetting during their sleep. Such a condition results in the caregivers having to frequently change and wash the affected bed sheets. Having to wash the bed sheets numerous times may damage the sheets and also requires the caregivers to cope with additional work load at home.

Some known products are directed to children that suffer from bedwetting. For example, disposable absorbent garments that target nocturnal enuresis sufferers may be used by children. Such known disposable absorbent garments are designed for children and may include pull on like features so that the child wearing them does not feel like he or she is wearing diapers. However, a significant percentage of the children who experience nocturnal enuresis (or their caregiver) reject using such disposable absorbent garments. For example, the child may feel embarrassed or are emotionally distressed by wearing a product that is similar to a diaper. Moreover, the garments may not adequately fit some of the older children.

Instead of wearing absorbent garments, many children or their caregivers may prefer to use, for example, disposable bed mats or pads. At least some known disposable bed mats or pads are designed to be placed under the bottom (or fitted) sheet of a bed. That is, some disposable bed mats or pads are designed to be placed between the bottom sheet and a mattress of the bed. While these bed mats or pads may prevent the mattress from being wetted, they do not provide any protection against the sheet becoming wet.

Other known disposable bed mats or pads are designed to be placed directly over the bottom sheets of a bed. When the child is positioned on the pad, insults by the child may be absorbed by the pad. However, such known bed pads may not be appropriately sized for the child's bed resulting in portions of the sheets still being affected by the insult. Further, some known pads do not have any adhesives and, therefore, may move on the bed. While some known bed pads include adhesive or means to increase the coefficient of friction between the pad and the bed, the adhesive may not attach to the sheets appropriately or the strength of the adhesive or the coefficient of friction may be insufficient and the pads may still continue to move on the bed. Moreover, at least some known pads are not sufficiently durable and the absorbent structure therein may readily tear during use, especially when used with an adhesive.

Other known products for protecting a bed include washable mattress pads, vinyl or plastic mattress covers, and absorbent towels or cloths. However, these products are typically placed between the fitted sheet and the mattress of the bed. As a result, if the child wets the bed the bottom sheet will not be protected. In addition, these products are more difficult to place and remove from the bed thereby limiting the child's independence in changing the pad. Instead, the child often has to rely on an older caregiver for help. Moreover, the known products are often not disposable thereby adding to the amount of laundry that needs to be done should the child wet the bed.

Therefore, there is a need in the art to provide children who experience bedwetting a disposable bed pad that is designed to fit various bed sizes, that uses sufficient adhesive to adhere the pad to a bed sheet such that the pad does not move during use and at the same time does not tear and/or cause other damage to the bed sheet, and that is sufficiently durable such that the pad does not tear readily.

SUMMARY

In one aspect, a disposable absorbent pad generally comprises an absorbent structure configured to absorb fluid. The disposable absorbent pad is adapted to provide a shear strength between the pad and the substrate when the pad is placed in engagement with the substrate between about 1,500 grams per square inch and about 3,500 grams per square inch.

In another aspect, a disposable absorbent pad for adhering to a substrate generally comprises an absorbent structure that is configured to absorb fluid. The disposable absorbent pad further comprises a back sheet having a first surface and a second surface. The second surface of the back sheet has an adhesive applied thereto for adhering the pad to a substrate. The adhesive covers between about 5 percent and about 100 percent of the second surface.

In yet another aspect, a disposable absorbent pad for adhering to a substrate generally comprises a top sheet, a back sheet and an absorbent structure configured to absorb fluid. The absorbent structure is disposed between the top sheet and the back sheet. The absorbent structure is attached to at least one of the top sheet and the back sheet. The attachment between the absorbent structure and the at least one of the top sheet and back sheet has an internal cohesive force between about 45 grams per square inch and about 100 grams per square inch.

BRIEF DESCRIPTION OF THE DRAWINGS

Corresponding reference characters indicate corresponding parts throughout the drawings.

DETAILED DESCRIPTION

Figure 6:
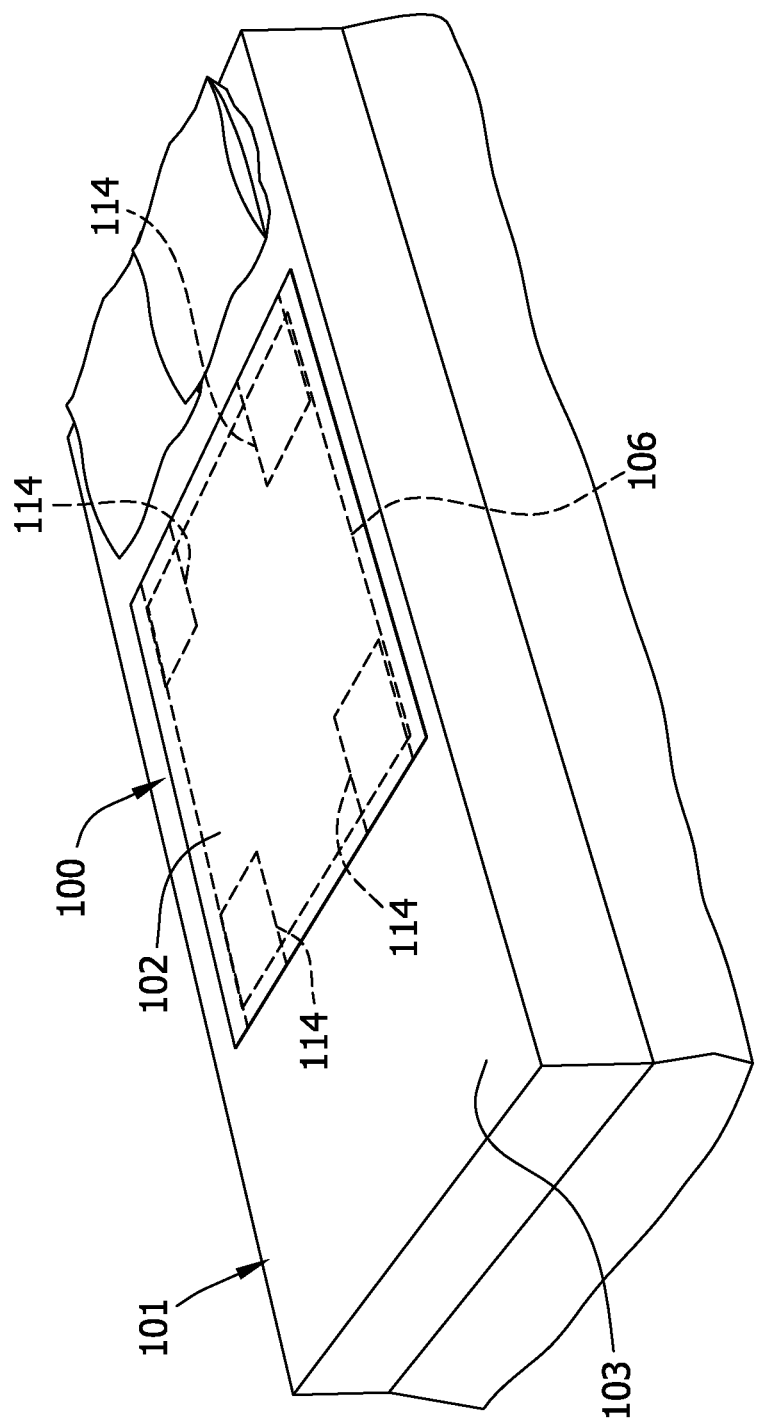
FIG. 6 is a perspective view of the disposable absorbent pad of FIG. 1 placed on a bed and attached to a bottom sheet thereof.
Figure 7A:
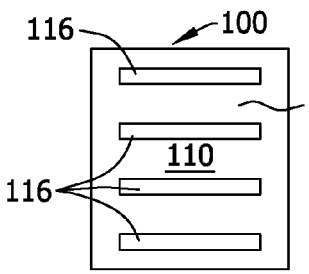
FIGS. 7A-7M are bottom views of the disposable absorbent pad illustrating suitable adhesive configurations.
Figure 7B:
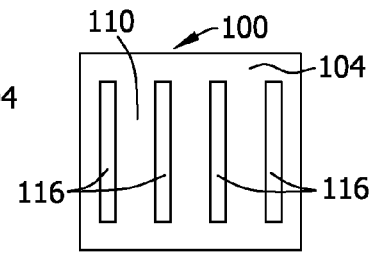
Figure 7C:
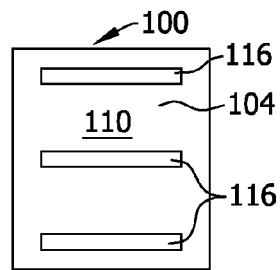
Figure 7D:
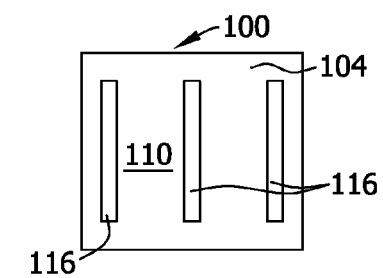
Figure 7E:
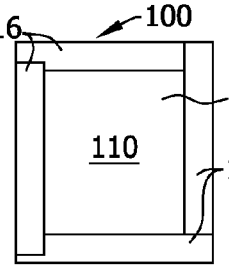
Figure 7F:
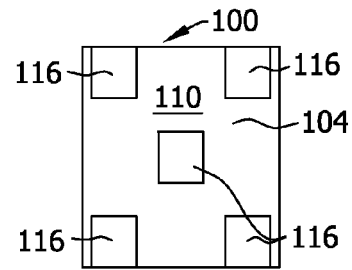
Figure 7G:
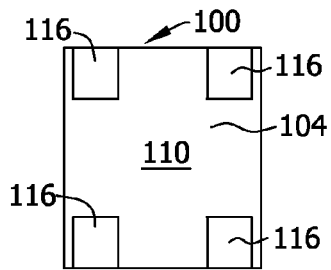
Figure 7H:
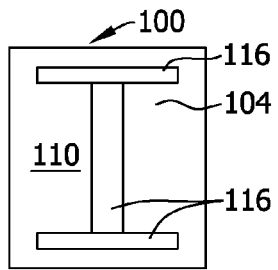
Figure 7I:
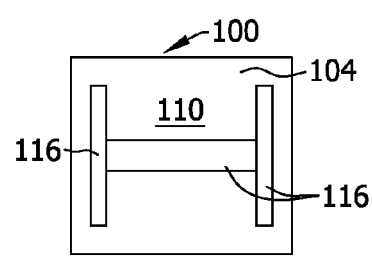
Figure 7J:
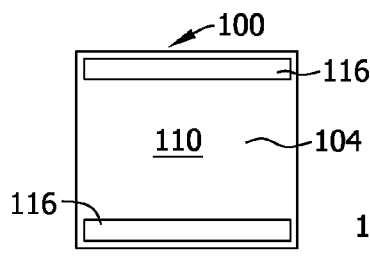
Figure 7K:
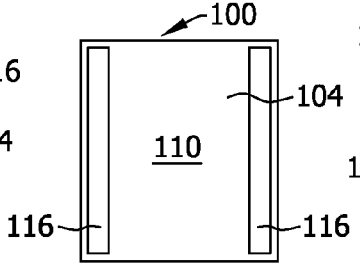
Figure 7L:
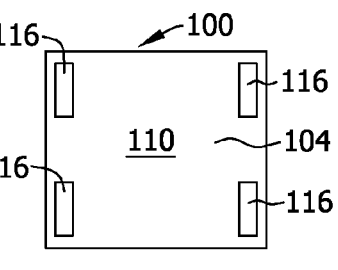
Figure 7M:
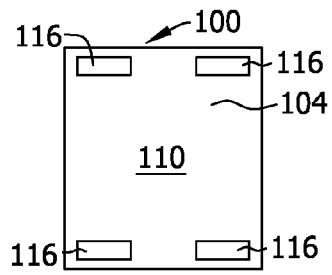

FIGS. 1-5 illustrate one suitable embodiment of a disposable absorbent pad, indicated generally at 100, configured to absorb fluid, such as bodily fluid. The illustrated disposable absorbent pad 100 is sized and shaped for placing on a bed 101 (FIG. 6). More specifically, the illustrated disposable absorbent pad 100 is adapted to be adhered to a bottom (e.g., a fitted) sheet 103 of the bed and underlie a child sleeping in the bed. Thus, as described in more detail below, the disposable absorbent pad 100 inhibits bodily fluid (e.g., urine) released from the child while sleeping in the bed 101 from wetting the bed sheet 103 or a mattress of the bed. It is understood that the disposable absorbent pad 100 can be placed between the bed sheet 103 and the mattress of the bed 101. In such a configuration, the disposable absorbent pad 100 can be adhered directly to the mattress. It is also understood that the disposable absorbent pad 100 can be used to inhibit other articles besides a bed from being contacted with the fluid. It is also understood that the disposable absorbent pad 100 can be used to absorb fluids besides urine, other bodily fluids, and other type of fluids (e.g., spilled drinks). It is further understood that the disposable absorbent pad 100 can be used for individuals besides children including, but not limited to, infants, elderly, and the bedridden. In addition, it is understood that the disposable absorbent pad 100 can be used for pets.

Figure 2:
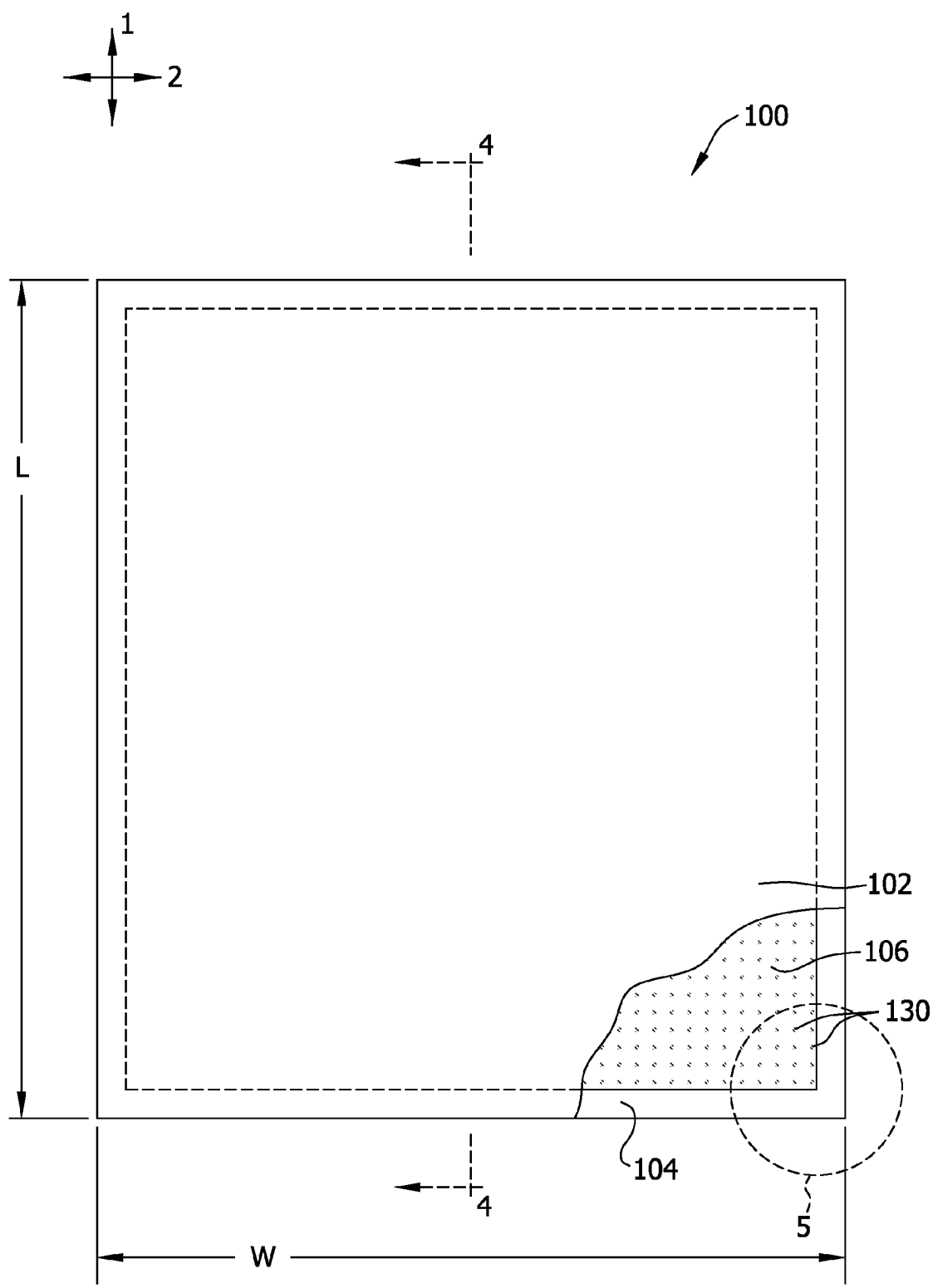
FIG. 2 is a top view of the disposable absorbent pad of FIG. 1 with a portion of a top sheet cut away to show an absorbent structure and a back sheet, both of which underlie the top sheet.
Figure 3:
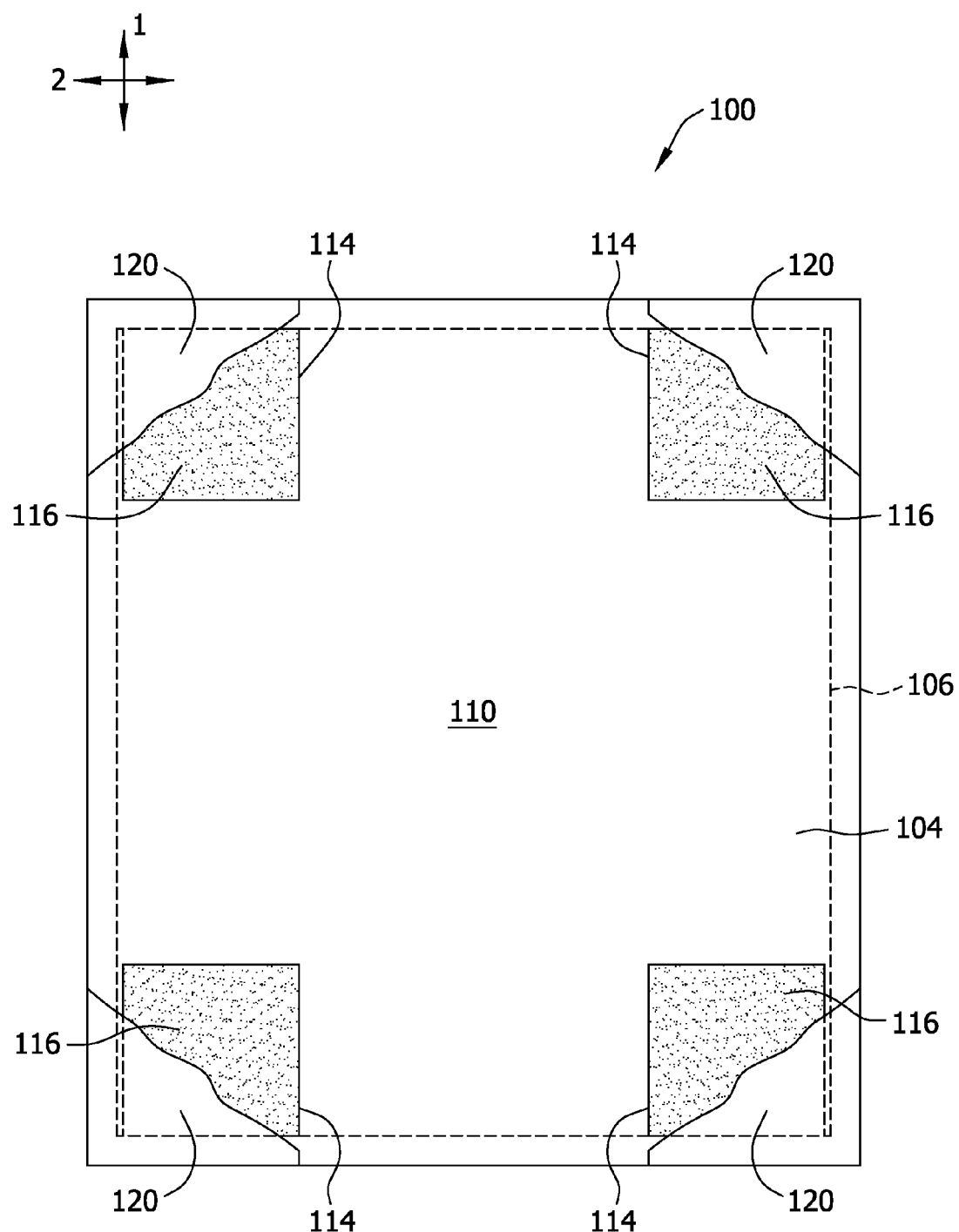
FIG. 3 is a bottom view of the disposable absorbent pad.

As seen in FIGS. 2 and 3, the disposable absorbent pad 100 has a longitudinal direction 1 and a lateral direction 2. The illustrated disposable absorbent pad 100, for example, has a length L (i.e., the extent of the disposable absorbent pad in the longitudinal direction 1) of approximately 880 millimeters and a width W (i.e., the extent of the disposable absorbent pad in the lateral direction 2) of approximately 780 millimeters. Thus, the illustrated disposable absorbent pad 100 is generally rectangular. It is understood that the pad 100 can have any suitable length and/or width. For example, the length of the disposable absorbent pad 100 can range from about 12 inches (305 millimeters) to about 84 inches (2,135 millimeters), and the width of the disposable absorbent pad can range from about 12 inches (305 millimeters) to about 72 inches (1,829 millimeters). It is also understood that the disposable absorbent pad 100 can have any suitable shape (e.g., square, circular, elliptical).

Figure 4:
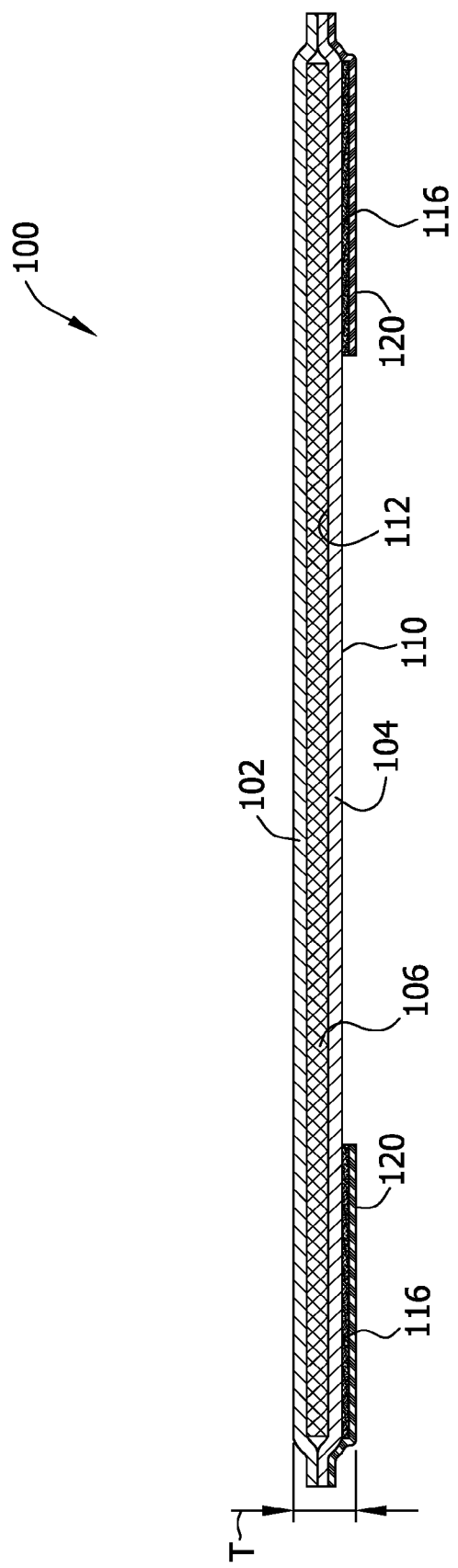
FIG. 4 is a cross-section taken along line 4-4 of FIG. 2.
Figure 5:
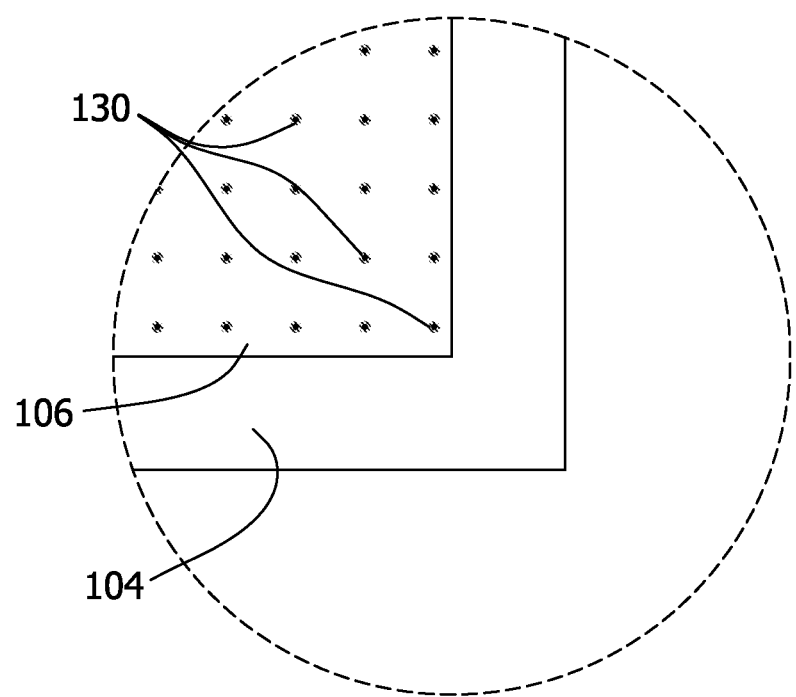
FIG. 5 is an enlarged view of a portion of the disposable absorbent pad circled in FIG. 2.

As illustrated in FIG. 4, the illustrated absorbent pad 100 includes a top sheet 102, a back sheet 104 and an absorbent structure 106 disposed between the top sheet and the back sheet. In the illustrated embodiment, the top sheet 102 and back sheet 104 extend beyond the periphery of the absorbent structure 106 and are adhesively bonded to each other to capture the absorbent structure. It is understood, however, that the top sheet 102 and back sheet 104 can be bonded together about the periphery of the absorbent structure 106 using any suitable bonding technique. It is also understood that the top sheet 102, back sheet 104, and absorbent structure 106 can be coextensive or that the top sheet and/or back sheet can have an extent less than the absorbent structure.

Figure 1:
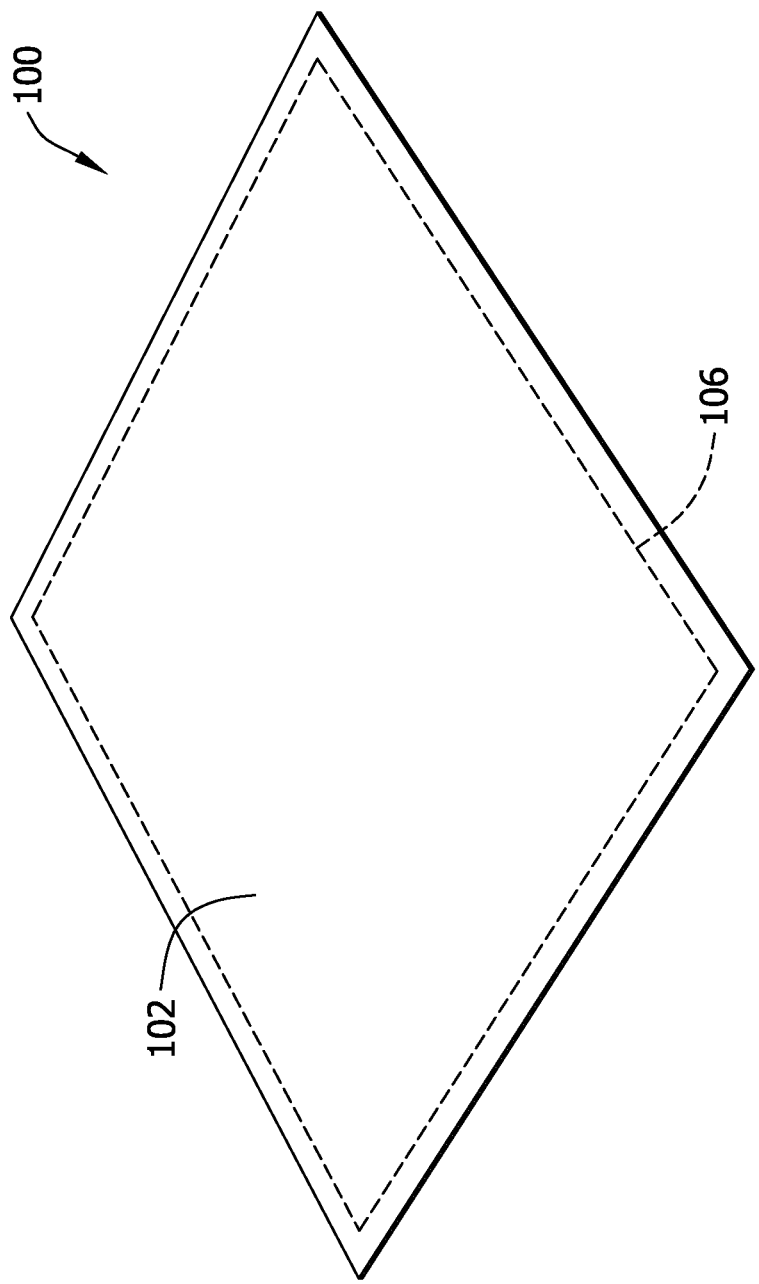
FIG. 1 is a perspective of one suitable embodiment of a disposable absorbent pad.

With reference now to FIGS. 1 and 2, the top sheet 102 comprises a liquid permeable material, which allows fluids to pass through the top sheet and into the underling absorbent structure 106. In one suitable embodiment, the top sheet 102 can be adapted to direct bodily fluids (e.g., urine) away from the child and toward the absorbent structure 106. That is, the top sheet 102 can be configured to retain little to no fluid in its structure and readily allow any bodily fluids to pass therethrough. Suitably, the top sheet 102 can be configured to provide a relatively comfortable and non-irritating surface for the child. Particularly, the illustrated top sheet 102 is configured to be relatively comfortable and non-irritating to the skin of the child.

The top sheet 102 can include a layer constructed of any operative material, and may be a composite material. For example, the top sheet 102 can include a woven fabric, a nonwoven fabric, a polymer film, a film-nonwoven fabric laminate or the like, as well as combinations thereof. Examples of a nonwoven fabric useable in the top sheet 102 include, for example, an airlaid nonwoven web, a spunbond nonwoven web, a meltblown nonwoven web, a bonded-carded web, a hydroentangled nonwoven web, a spunlace web or the like, as well as combinations thereof. Other examples of suitable materials for constructing the top sheet 102 can include rayon, bonded-carded webs of polyester, polypropylene, polyethylene, nylon, or other heat-bondable fibers, finely perforated film webs, net-like materials, and the like, as well as combinations thereof. These webs can be prepared from polymeric materials such as, for example, polyolefins, such as polypropylene and polyethylene and copolymers thereof, polyesters in general including aliphatic esters such as polylactic acid, nylon or any other heat-bondable materials. When the top sheet 102 is a film or a film laminate, the film should be sufficiently apertured or otherwise be made to allow fluids to flow through the top sheet to the absorbent structure 106.

Other examples of suitable materials for the top sheet 102 are composite materials of a polymer and a nonwoven fabric material. The composite materials are typically in the form of integral sheets generally formed by the extrusion of a polymer onto a nonwoven web, such as a spunbond material. In a particular arrangement, the top sheet 102 can be configured to be operatively liquid-permeable with regard to the liquids that the pad is intended to absorb or otherwise handle. The operative liquid-permeability may, for example, be provided by a plurality of pores, perforations, apertures or other openings, as well as combinations thereof, that are present or formed in the top sheet 102. The apertures or other openings can help increase the rate at which bodily fluid (e.g., urine) can move through the thickness of the top sheet 102 and penetrate into the absorbent structure 106.

In the illustrated embodiment, the top sheet 102 extends beyond the absorbent structure 106 and is adhesively bonded to the back sheet 104. It is contemplated, however, that the top sheet 102 can have the same extent as the absorbent structure 106 and/or back sheet 104 or can have an extent less that the absorbent structure and/or back sheet. It is further contemplated that in some embodiments (not shown), the top sheet 102 can be omitted. Thus, in such an embodiment, the disposable absorbent pad 100 would comprise the absorbent structure 106 and the back sheet 104.

With reference again to FIG. 4, the absorbent structure 106 is configured to absorb body fluids including, but not limited to, urine that passes through the top sheet 102. The absorbent structure 106 may have one or more layers of absorbent materials. That is, the absorbent structure 106 may be a single layer of absorbent materials or may be a multilayer structure.

Each of the layers of the absorbent structure 106 can contain similar materials or different materials.

Suitable materials which can be used to form the absorbent structure 106 include those materials conventionally used in absorbent pads and include materials, such as, for example, cellulose, wood pulp fluff, rayon, cotton, and meltblown polymers such as polyester, polypropylene or coform. Coform is a meltblown air-formed combination of meltblown polymers, such as polypropylene, and absorbent staple fibers, such as cellulose.

The absorbent structure 106 can also be formed from a composite comprised of a hydrophilic material which may be formed from various natural or synthetic fibers, wood pulp fibers, regenerated cellulose or cotton fibers, or a blend of pulp and other fibers. One particular example of a material which may be used as the absorbent structure is an airlaid material.

In one suitable embodiment, the absorbent structure 106 may include a superabsorbent material, in addition to or in place of the hydrophilic material, which increases the ability of the absorbent structure to absorb a large amount of fluid in relation to its own weight. Generally stated, the superabsorbent material can be a water-swellable, generally water-insoluble, hydrogel-forming polymeric absorbent material, which is capable of absorbing at least about 15, suitably about 30, and possibly about 60 times or more its weight in physiological saline (e.g., saline with 0.9 wt % NaCl). The superabsorbent materials can be inserted into the absorbent structure 106 as particles or in sheet form. The superabsorbent material may be biodegradable or bipolar. In one suitable embodiment, the superabsorbent material may be uniformly distributed or selectively placed within the absorbent structure 106 to prohibit leakage. The amount of superabsorbent material may be selected to hold an anticipated quantity of liquid such as urine, for instance during over-night usage. The amount of superabsorbent material may, for example, be from about 5 grams to about 100 grams of a highly absorbent polyacrylate.

The hydrogel-forming polymeric absorbent material may be formed from organic hydrogel-forming polymeric material, which may include natural material such as agar, pectin, and guar gum; modified natural materials such as carboxymethyl cellulose, carboxyethyl cellulose, and hydroxypropyl cellulose; and synthetic hydrogel-forming polymers. Synthetic hydrogel-forming polymers include, for example, alkali metal salts of polyacrylic acid, polyacrylamides, polyvinyl alcohol, ethylene maleic anhydride copolymers, polyvinyl ethers, polyvinyl morpholinone, polymers and copolymers of vinyl sulfonic acid, polyacrylates, polyacrylamides, polyvinyl pyridine, and the like. Other suitable hydrogel-forming polymers include hydrolyzed acrylonitrile grafted starch, acrylic acid grafted starch, and isobutylene maleic anhydride copolymers and mixtures thereof. The hydrogel-forming polymers may be lightly crosslinked to render the material substantially water insoluble. Crosslinking may, for example, be by irradiation or covalent, ionic, Van der Waals, or hydrogen bonding. Hydroxyfunctional polymers have been found to be good superabsorbents for sanitary napkins. Such superabsorbents are commercially available from Dow Chemical, Hoechst-Celanese, and Stockhausen, Incorporated, among others, and are a partially neutralized salt of cross-linked copolymer of polyacrylic acid and polyvinyl alcohol having an absorbency under load value above 25 grams of absorbed liquid per gram of absorbent material (g/g). Other types of superabsorbent materials known to those skilled in the art can also be used.

Additional layers or substrates, such as, a liquid acquisition and distribution layer, also referred to as a surge or transfer layer, and an optional tissue layer can be incorporated into the absorbent structure 106 of the absorbent pad 100. The distribution layer may be shorter than the absorbent structure 106 or have the same length as the absorbent structure. The distribution layer serves to temporarily hold an insulting fluid to allow the absorbent structure sufficient time to absorb the fluid, especially when a superabsorbent material is present.

The back sheet 104 is generally liquid impermeable and is attached to the absorbent structure 106 to prevent fluid entering the absorbent structure 106 from flowing through the absorbent structure and onto the substrate (e.g., bed sheet 103 of FIG. 6) to which the disposable absorbent pad 100 is adhered. More specifically, the back sheet 104 has an outer surface 110 and an opposing inner surface 112. As illustrated in FIG. 4, the absorbent structure 106 is attached (e.g., adhesively bonded) to the inner surface 112 of the back sheet 104. It is understood that the substrate to which the disposable absorbent pad 100 is adhered can be any suitable substrate including, but not limited to, bed sheets (cotton, fleece, cotton/synthetic fiber blends, bamboo), mattresses, bet mats, chairs, sofas, car seats, and floors (carpet, vinyl covering, wood flooring).

The liquid impermeable back sheet 104 may be a polymeric film, a woven fabric, a nonwoven fabric or the like, as well as combinations or composites thereof. For example, the liquid impermeable back sheet 104 may include a polymer film laminated to a woven or nonwoven fabric. The polymer film can be composed of polyethylene, polypropylene, polyester, silicone or the like, as well as combinations thereof. Additionally, the polymer film may be micro-embossed, have a printed design, have a printed message to the consumer, and/or may be at least partially colored.

The back sheet 104 may be made from a liquid/moisture permeable material that is rendered moisture proof by means of hydrophobic additives. It is understood that back sheet 104 can be made from a fibrous (e.g., a nonwoven) material or other suitable permeable material. In such an embodiment, the disposable absorbent pad 100 may include a suitable barrier layer.

In the illustrated embodiment, the absorbent structure 106 is adhesively bonded to both the top sheet 102 and the back sheet 104. In addition, the top sheet 102 is adhesively bonded to the back sheet 104 about the periphery of the absorbent structure 106. It is contemplated that the top sheet 102, the back sheet 104, and absorbent structure 106 can be bonded together using other suitable bonding techniques besides adhesive. It is also contemplated that the top sheet 102 can be free from direct bonding with either the back sheet 104 or the absorbent structure 106, or that the back sheet can be free from direct bonding with either the top sheet or the absorbent structure.

The absorbent structure 106 includes pattern bonding defined by a plurality of point bonds 130. While the point bonds 130 can have various sizes and shape, in one suitable embodiment, the bond points are generally circular and have a diameter of less than about 10 millimeters and suitably, between about 0.5 millimeters and about 3 millimeters. For example, the bond points 130 can have a diameter of approximately 1 millimeter. It is understood, however, that the bond points can have any suitable size or shape. In one suitable embodiment, the point bonds 130 may be formed by embossing dots (broadly "embossing elements") in the absorbent structure 106. In the illustrated embodiment, the point bonds 130 are generally aligned in lateral and longitudinal extending rows. It is understood, however, that the point bonds 130 can be arranged in any suitable pattern.

In one suitable embodiment, more than 1 percent of the absorbent structure 106 is bonded by the point bonds 130. Suitably, 10 percent to 60 percent of the absorbent structure 106 is bonded by the point bonds 130. More suitably, 15 percent to 45 percent of the absorbent structure 106 is bonded by the point bonds 130. In one suitable embodiment, for example, approximately 17.5 percent of the absorbent structure 106 is bonded by the point bonds 130.

It is understood that the pattern bonding can be formed using any suitable pattern including continuous and discontinuous patterns. For example, the pattern bonding can comprise the discontinuous point bonds 130 illustrated herein or can include a continuous line diamond pattern. It is also understood that the pattern bonding can be in the form of a decorative figure, e.g., an animal, a cartoon character, or other playful character. It is contemplated that the pattern bonding could be achieved in any suitable manner including heated rollers, ambient temperature rollers, or ultrasonic bonding.

As seen in FIG. 3, the illustrated top sheet 102 and back sheet 104 is free from the point bonds 130. That is, neither the top sheet 102 nor the back sheet 104 is point bonded to the absorbent structure 106. Rather, in the illustrated embodiment, top sheet 102, the back sheet 104 and the absorbent structure is adhesively bonded together. It is contemplated, however, that the back sheet 104 can be bonded to the top sheet 102 and/or the absorbent structure 106 in other suitable ways (including point bonding), and that the top sheet can be bonded to the back sheet 104 and/or the absorbent structure in other suitable ways (including point bonding).

As illustrated in FIG. 3, the outer surface 110 of the back sheet 104 includes at least one area 114 having adhesive 116 applied thereto. More specifically, in the illustrated exemplary embodiment, the outer surface 110 of the back sheet 104 includes four areas 114 having adhesive 116 applied thereto. As seen in FIG. 3, each of the four areas 114 is positioned generally adjacent the corners of the outer surface 110 of the back sheet 104. It is contemplated that the outer surface 110 of the back sheet 104 can have more or fewer areas 114 of adhesive 116 than the four areas of adhesive illustrated in FIG. 3. It is also contemplated that the adhesive 116 can be applied to other portions of the outer surface 110. Thus, the adhesive 116 can be applied to portions of the outer surface 110 spaced from its corners.

In one suitable embodiment, the adhesive 116 covers between about 5 percent and about 100 percent of the outer surface 110 of the back sheet 104 of the disposable absorbent pad 100. Preferably, the adhesive 116 covers between about 10 percent and about 60 percent of the outer surface 110, and more preferably between about 10 percent and about 40 percent of the outer surface, and even more preferably the adhesive covers about 16 percent of the outer surface.

In one suitable embodiment, the adhesive 116 is applied to the outer surface 110 of the back sheet 104 in a range between about 10 grams per square meter (gsm) and about 60 gsm. Suitably, approximately 40±5 gsm of adhesive 116 is applied to the outer surface 110 of the back sheet 104. It is understood, however, that the quantity of adhesive 116 applied to the back sheet 104 can differ from those disclosed herein. Rather, any suitable quantity of adhesive 116 can be applied to the outer surface 110 of the back sheet 104.

In the illustrated embodiment, each area 114 of adhesive 116 has a substantially rectangular shape. It is contemplated, however, that each of the areas 114 of adhesive 116 may have any suitable shape and/or size. It is also contemplated that the adhesive 116 can be applied to the outer surface 110 of the back sheet 104 in a pattern (e.g., strips, dots). Various suitable adhesive 116 configurations for the disposable absorbent pad 100 are illustrated in FIGS. 7A-7M.

In one suitable embodiment, the adhesive 116 is an adhesive that enables the disposable absorbent pad 100 to be removably attached to the bed sheet 103. That is, the adhesive 116 enables the disposable absorbent pad 100 to be held in place on the bed sheet 103 during use and the disposable absorbent pad may be readily removed from the bed sheet after use. Suitably, little or no residual adhesive 116 will remain on the bed sheet 103 after the disposable absorbent pad 100 is removed therefrom. It is also preferred that the adhesive 116 does not permanently or temporarily mark or otherwise discolor the bed sheet 103. Several suitable adhesives are available from HB Fuller with an office in St. Paul, Minn., U.S.A. and available under product numbers 1827S and CHM-1056ZP.

A release strip or a peel strip 120 may be used to cover the adhesive 116 and thereby prevent the adhesive from becoming contaminated, thus losing its ability to stick to the bed sheet 103 and/or prematurely adhering to itself or an unintended surface. A portion of the peel strip 120 covering the adhesive 116 applied to the outer surface 110 of the back sheet 104 is illustrated in FIG. 3. Suitable materials for use as the peel strip 120 are well known in the art and are commercially available. Examples of suitable peel strip 120 materials include, a silicone coated Kraft paper, a silicone coated film or the like. Other coatings suitable for use in the peel strip 120 include coatings containing polytetrafluoroethylene.

In one suitable embodiment, the adhesive 116 is configured to provide a shear strength between the disposable absorbent pad 100 and the bed sheet 103 when the absorbent pad is adhered to the bed sheet between about 1,500 grams per square inch and about 3,500 grams per square inch. Suitably, the adhesive 116 is configured to provide a shear strength between about 2,000 grams per square inch and about 3,000 grams per square inch. More suitably, the adhesive 116 is configured to provide a shear strength between about 2,200 grams per square inch and about 2,500 grams per square inch.

It is contemplated that the disposable absorbent pad 100 can be adapted to provide the shear strength between the pad and the substrate in other suitable ways besides adhesive. For example, the pad 100 can include mechanical fasteners (e.g., hook and loop fasteners, slot and tab, magnets) to provide suitable shear strength between the pad 100 and the substrate. In another suitable example, the back sheet 104 of the pad 100 can comprise a high coefficient of friction material. In such an embodiment, the high coefficient of friction material of the back sheet 104 of the pad 100 would provide the shear strength between the pad and the substrate.

The adhesive 116 is also configured to provide a peel strength between the absorbent pad 100 and the bed sheet 103 when the absorbent pad is adhered to the bed sheet between about 200 grams per inch and about 500 grams per inch. Suitably, the adhesive 116 is configured to provide a peel strength between about 250 grams per inch and about 450 grams per inch. More suitably, the adhesive 116 is configured to provide a peel strength between about 300 grams per inch and about 350 grams per inch.

The attachment between the absorbent structure 106 and the top sheet 102 and/or the back sheet 104 has an internal cohesive force of between about 45 grams per square inch and about 100 grams per square inch. Suitably, the attachment between the absorbent structure 106 and the top sheet 102 and/or the back sheet 104 has an internal cohesive force between about 55 grams per square inch and about 80 grams per square inch, more suitably, about 64 grams per square inch.

In one suitable embodiment, the disposable absorbent pad 100 is relatively thin. Suitably, the disposable absorbent pad 100 has a total thickness T less than about 1.5 millimeters and more suitably less than about 1 millimeter (FIG. 4). In one suitable example, the total thickness T of the disposable absorbent pad 100 is about 0.9 millimeters. It is understood that the disposable absorbent pad can have other total thicknesses.

In one suitable embodiment, the disposable absorbent pad 100 is relatively stiff. Suitably, the disposable absorbent pad 100 has a Gurley stiffness between about 60 milligrams of force and about 80 milligrams of force. In one suitable example, the Gurley stiffness of the disposable absorbent pad 100 is about 72 milligrams of force. It is understood that the disposable absorbent pad can have other Gurley stiffnesses.

In one suitable embodiment, a ratio of Gurley stiffness to thickness is between about 40 mg/mm and about 100 mg/mm and more suitably between about 60 mg/mm and about 90 mg/mm and even more suitable between about 75 mg/mm and about 85 mg/mm. In one suitable example, the ratio of Gurley stiffness to thickness is approximately 84 mg/mm.

The disposable absorbent pad 100 described above can be an individual absorbent pad or may be part of an absorbent pad system, offering the user a wide variety of options to fill the needs of the user. For example, the pad system could provide users pads in a variety of shapes or sizes to allow users to select the appropriate shape or size for the various substrates that users intend to use with the pad. Likewise, the adhesive 116 may be provided in a variety of adhesive strengths to match the adhesive strength needed or desired by the user. Similarly, the absorbent structure 106 could be provided in various absorbent capacities so that the user could select the appropriate absorbency to match the user's needs.

The disposable absorbent pads and/or the absorbent pad system may be provided to users in a variety of packaging arrangements. In one packaging arrangement for the pad system, a plurality of pads having different properties may be provided in separate packages or could be provided in a single package. Generally, however, it is preferred to package a plurality of disposable absorbent pads 100 having similar properties, shapes and/or sizes in a single package.

In use, the child or a caregiver removes the peel strips 120 covering each of the areas 114 of adhesive 116 applied to the outer surface 110 of the back sheet 104. The child/caregiver then adheres the disposable absorbent pad 100 to the bed sheet 103 of the bed 101 such that the pad overlies the sheet and the mattress in an area generally aligned with the torso of the child when the child in is lying in the bed. Thus, when the child sleeps on the bed 101, the disposable absorbent pad 100 is suitably positioned directly beneath the child to receive and absorb any bodily fluids (i.e., urine) released by the child while the child sleeps. As a result, the disposable absorbent pad 100 inhibits urine released by the child from wetting the bed sheet 103 and the mattress of the bed 101. The disposable absorbent pad 100 can be removed from the bed sheet 103 by the child or caregiver manually peeling the pad from the sheet.

The bed sheet 103 may be a flat or fitted type of sheet. In the illustrated embodiment, for example, the bed sheet 103 is a fitted sheet. Moreover, the bed sheet 103 may be made of any material suitable for bed sheets, including but not limited to cotton, flannel, linen, satin, silk, rayon, bamboo fiber, and as well as any combinations thereof.

In one suitable method, the illustrated absorbent structure 106 can be made by distributing cellulose fluff uniformly onto a tissue paper layer. Next, particles of suitable super absorbent material (SAM) are generally uniformly distributed onto the fluff. Then another layer of tissue paper is placed over the cellulose fluff containing the SAM to form a composite. The composite is then compacted using any suitable means. In one example, the composite can be directed through a steel/steel nip. In one suitable embodiment, the steel/steel nip comprises an embossing roll and an associated anvil roll. Suitably, at least one of the embossing roll and the anvil roll are heated and, more suitably, both the embossing roll and the anvil roll are heated.

It is contemplated that the absorbent structure 106 can be formed as a continuous web or as discrete unit. If the absorbent structure 106 is formed as a continuous web comprising a plurality of interconnected absorbent structure, the method of forming the absorbent structure could include a suitable device to cut the interconnected absorbent structures into discrete piece. For example, one suitable cutting device is knife and associated anvil roll.

To form the illustrated disposable absorbent pad 100, the discrete absorbent structures 106 are placed on a continuous web to which adhesive has been uniformly applied. In one suitable embodiment, the continuous web is material suitable for the back sheet 104. Next, a continuous web of nonwoven material (or other material suitable for use as the top sheet 102), which has adhesive applied thereto, is then laid over the absorbent structure 106. The continuous webs cores are adhesively bonded to the discrete absorbent structures 106 and to each other about the periphery of the absorbent structure thereby capturing each of the absorbent structures. The resulting laminate structure is them passed through a suitable nip (e.g., a rubber/steel nip) to assure pad integrity.

The adhesive 116, which is suitably a pressure sensitive adhesive, is discontinuously applied to two continuous webs of release paper (e.g., material suitable for making peel strip 120). The web with the adhesive applied thereto is then cut and applied using a nip roller to the laminate structure such that the web pieces span between two absorbent pads. Laminate structure is then cut into discreet disposable absorbent pads, which are then folded and packaged. The disposable absorbent pads 100 can be packaged as a single unit or a plurality of disposable absorbent pads can be packaged together.

EXPERIMENTS

Experiment 1

In this experiment, the absorbent pad 100 using the adhesive 116 was tested and compared to two known absorbent pads to identify the shear strength that is provided by adhesive 116 between the disposable absorbent pad 100 and a cotton sheet when the absorbent pad is adhered to the cotton sheet. The known absorbent pads that were used for comparison in this experiment include the Peach Sheet Underpad available from Tranquility® Incontinence Products of Dunbridge, Ohio, U.S.A. and the StaPut Flat Adhesive Underpad available from Kimberly-Clark Professional of Roswell, Ga., U.S.A.

Five different pads for each of the Tranquility bed pads and the Kimberly-Clark Professional bed pads, and three different pads for the absorbent pad 100 were attached onto a cotton bed sheet to determine the shear strength provided by the adhesives used by each pads. More specifically, a modified Test Method of STM 5556 was performed with a 2"×6"

sample of poly containing adhesive applied to a cotton fabric. The sample was rolled with a 2 kg weight and then the poly with adhesive was placed in the top jaw while the fabric was placed in the lower jaw. The jaws were then pulled apart at a rate of 20 in/min. The sample was pulled apart until a break occurred or the poly released from the cotton fabric. The samples from the Tranquility and Kimberly-Clark professional bed pads did not have a large enough adhesive area to cover the 2" dimension. As a result, the samples from the Tranquility and Kimberly-Clark professional bed pads were cut such that the adhesive was centered across the 2" dimension and the results were normalized to provide a force per square inch equivalent.

TABLE 1

Figure 8:
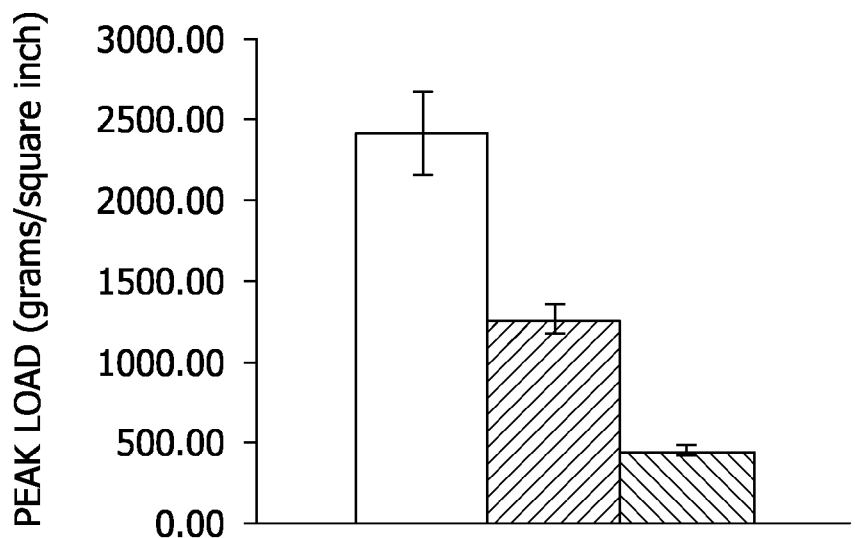
FIG. 8 is a graph depicting the results of a normalized shear strength experiment.

Data results that correspond to FIG. 8 and include the results from testing the normalized shear strength for each type of pad.

| Product Type | Specimen No. | Peak Load (grams/sq. in.) |
|---|---|---|
| The Absorbent Pad Described Herein | 1 | 2430 |
| | 2 | 2172.33 |
| | 3 | 2672.08 |
| | Ave. | 2424.81 |
| | Std. | 249.92 |
| Tranquility Peach Sheet Pad | 1 | 1416.75 |
| | 2 | 1179.5 |
| | 3 | 1208.4 |
| | 4 | 1285.35 |
| | 5 | 1275.95 |
| | Ave. | 1273.19 |
| | Std. | 91.84 |
| Kimberly-Clark Professional Bed Pads | 1 | 434.5 |
| | 2 | 491.2 |
| | 3 | 452.9 |
| | 4 | 441.73 |
| | 5 | 481.15 |
| | Ave. | 460.30 |
| | Std. | 24.77 |

As illustrated in Table 1 and FIG. 8, the disposable absorbent pad 100 described herein has a substantially higher normalized shear strength than the known bed pads. More specifically, the disposable absorbent pad 100 had a normalized shear strength ranging from 2172.33 grams per square inch to 2672.08 grams per square inch, with an average of 2424.81 grams per square inch. The normalized shear strength of the disposable absorbent pad 100, which is provided by the adhesive 116 applied to the outer surface 110 of the back sheet 104, is substantially greater than the normalized shear strength of the Tranquility bed pads and the Kimberly-Clark Professional bed pads.

Experiment 2

In this experiment, five different pads for each of the absorbent pads 100, the Tranquility bed pads, and the Kimberly-Clark Professional bed pads were attached onto a cotton bed sheet to determine the peel strength provided by the adhesive used by each. More specifically, a modified test method of STM-5571 was performed with a 2" wide sample of poly containing adhesive applied to cotton fabric. The sample was rolled with a 2 kg weight and then the poly containing adhesive was placed in the top jaw while the fabric was placed in the lower jaw. The jaws were then pulled apart at a speed of 20 in/min. The test end point was set at 8" whereas the data logging limits were set between 1" and 7". The average force was calculated over this area. The samples from the Tranquility and Kimberly-Clark professional bed pads did not have a large enough adhesive area to cover the 2" width. As a result, the samples from the Tranquility and Kimberly-Clark professional bed pads were cut such that the adhesive was centered across the 2" width and the results were normalized to provide a force per square inch equivalent.

TABLE 2

Figure 9:
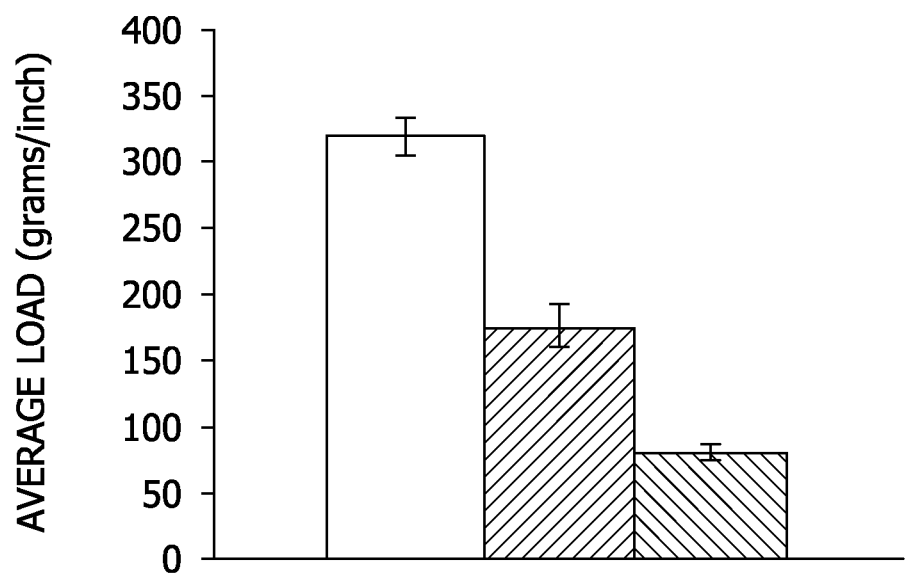
FIG. 9 is a graph depicting the results of a normalized peel strength experiment.

Data results that correspond to FIG. 9 and include the normalized results from testing the normalized peel strength for each type of pad.

| Product Type | Specimen No. | Average Load (grams/in.) |
|---|---|---|
| The Absorbent Pad Described Herein | 1 | 315.95 |
| | 2 | 337.9 |
| | 3 | 318.95 |
| | 4 | 298.75 |
| | 5 | 326.35 |
| | Ave. | 319.58 |
| | Std. | 14.39 |
| Tranquility Peach Sheet Pad | 1 | 182.5 |
| | 2 | 200.2 |
| | 3 | 161.2 |
| | 4 | 166 |
| | 5 | 169.6 |
| | Ave. | 175.30 |
| | Std. | 15.71 |
| Kimberly-Clark Professional Bed Pads | 1 | 88.06 |
| | 2 | 82.88 |
| | 3 | 85.68 |
| | 4 | 75.6 |
| | 5 | 75.04 |
| | Ave. | 81.45 |
| | Std. | 5.89 |

As illustrated in Table 2 and FIG. 9, the disposable absorbent pad 100 had a normalized average peel strength ranging from 298.75 grams per inch to 337.9 grams per inch, with an average of 319.58 grams per inch. The normalized peel strength of the disposable absorbent pad 100, which is provided by adhesive 116 applied to the outer surface 110 of the back sheet 104, is substantially greater than the normalized peel strength of the Tranquility bed pads and the Kimberly-Clark Professional bed pads.

Experiment 3

In this experiment, five different pads for each of the absorbent pads 100, the Tranquility bed pads, and the Kimberly-Clark Professional bed pads were attached onto a cotton bed sheet to determine the cohesive force between the cotton bed sheet and the adhesives used by each. More specifically, the standard cohesion test method was performed with a 2"×4" sample of poly containing adhesive. The poly containing adhesive was then attached to a cotton fabric and a piece of 2 sided tape attached the fabric and a bottom of the tester. They were then pressed together with 60 psi of pressure for approximately 3 seconds. Another piece of 2 sided tape was then added to a 1"×1" square and this was attached to the top poly containing adhesive with 60 psi of pressure for 10 seconds. They were then pulled apart and a value was recorded based on how much force was required to release the adhesive from its cotton substrate. The Kimberly-Clark Professional bed pad did not have a large enough adhesive area to create 1"×1" square samples that were covered by adhesive. As a result, 1"×1" samples were cut from the Kimberly-Clark Professional bed pad such that the available adhesive was centered across the 1"×1" sample and the results were normalized to provide a force per square inch equivalent.

TABLE 3

Figure 10:
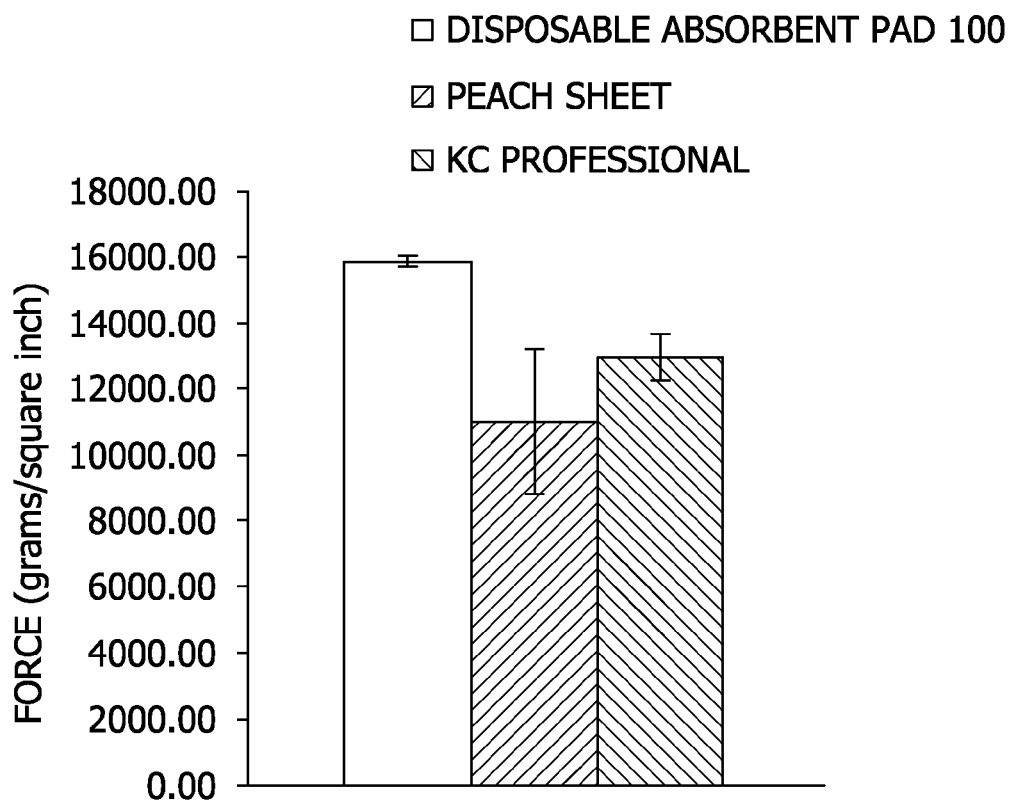
FIG. 10 is a graph depicting the results of a cohesive force experiment testing the cohesion between adhesive on the back sheet of the disposable absorbent pad and a substrate.

Data results that correspond to FIG. 10 and include the normalized results from testing the cohesive force between each pad and a substrate.

| Product Type | Specimen No. | Normalized Force (grams/sq. in.) | Mode of Failure |
|---|---|---|---|
| The Absorbent Pad Described Herein | 1 | 15740 | Adhesive Poly Tear |
|  | 2 | 16080 | Adhesive Poly Tear |
|  | 3 | 15740 | Material from Top |
|  | 4 | 15740 | Top Tape Released |
|  | 5 | 16060 | Top Tape Released |
|  | Ave. | 15872 |  |
|  | Std. | 180 |  |
| Tranquility Peach Sheet Pad | 1 | 14740 | Tape from poly |
|  | 2 | 8940 | Tape from poly |
|  | 3 | 11280 | Tape from poly |
|  | 4 | 10420 | Tape from poly |
|  | 5 | 9860 | Tape from poly |
|  | Ave. | 11048 |  |
|  | Std. | 2232 |  |
| Kimberly-Clark Professional Bed Pads | 1 | 1244 | Film from material |
|  | 2 | 11950 | Film from material |
|  | 3 | 13540 | Film from material |
|  | 4 | 13540 | Film from material |
|  | 5 | 13290 | Film from material |
|  | Ave. | 12952 |  |
|  | Std. | 719 |  |

As illustrated in Table 3 and FIG. 10, the disposable absorbent pad 100 has a substantially higher cohesive force between the pad and a substrate than the known bed pads. More specifically, the disposable absorbent pad 100 had an average normalized cohesive force ranging from 15740 grams per square inch to 16080 grams per square inch, with an average of 15872 grams per square inch.

Experiment 4

In this experiment, five different pads for each of the absorbent pads 100, the Tranquility bed pads, and the Kimberly-Clark Professional bed pads were tested for stiffness. More specifically, each of the pads was tested using a standard Gurley Stiffness test with a 1"×1" sample size.

TABLE 4

Figure 11:
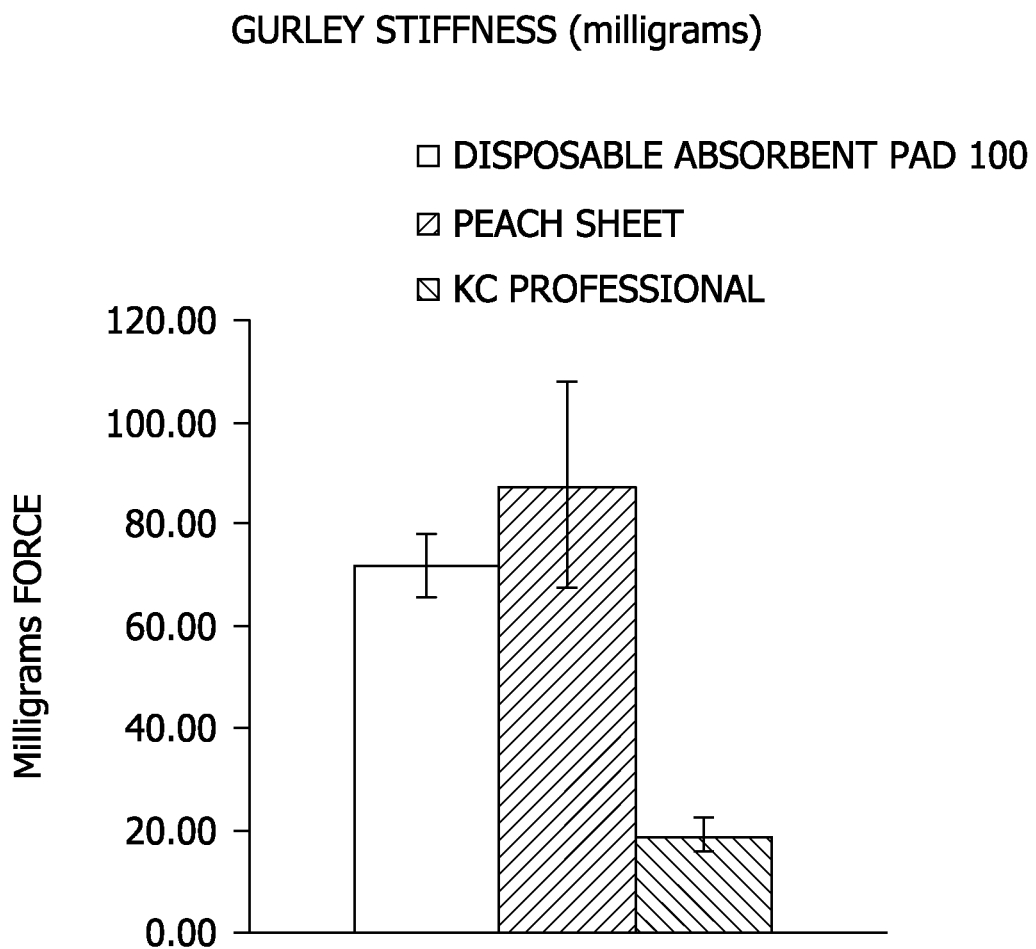
FIG. 11 is a graph depicting the results of a Gurley stiffness test.

Data results that correspond to FIG. 11 and include the results from testing the Gurley stiffness of each pad.

| Product Type | Specimen No. | Gurley Stiffness (mg Force) |
|---|---|---|
| The Absorbent Pad Described Herein | 1 | 72.28 |
|  | 2 | 80.62 |
|  | 3 | 69.50 |
|  | 4 | 73.67 |
|  | 5 | 63.94 |
|  | Ave. | 72 |
|  | Std. | 6.09 |
| Tranquility Peach Sheet Pad | 1 | 76.45 |
|  | 2 | 73.67 |
|  | 3 | 84.79 |
|  | 4 | 123.71 |
|  | 5 | 80.60 |
|  | Ave. | 87.84 |
|  | Std. | 20.49 |
| Kimberly-Clark Professional Bed Pads | 1 | 17.20 |
|  | 2 | 24.42 |
|  | 3 | 16.65 |
|  | 4 | 21.09 |
|  | 5 | 16.65 |
|  | Ave. | 19.20 |
|  | Std. | 3.46 |

As illustrated in Table 4 and FIG. 11, the absorbent pad 100 is substantially stiffer than the Kimberly-Clark Professional bed pads. Moreover, the absorbent pad 100 has a Gurley stiffness that is generally comparable to the Tranquility bed pads.

Experiment 5

In this experiment, five different pads for each of the absorbent pads 100, the Tranquility bed pads, and the Kimberly-Clark Professional bed pads were tested for thickness. More specifically, the middle portion of each pad (e.g., the area of the pad where a child would typically sleep) was tested. The measurements were done with a probe with a 3" diameter brass circle plate on the bottom (i.e., not a point probe). Measurements were taken at various locations in the middle portion of the pad and the thickness was recorded.

TABLE 5

Figure 12:
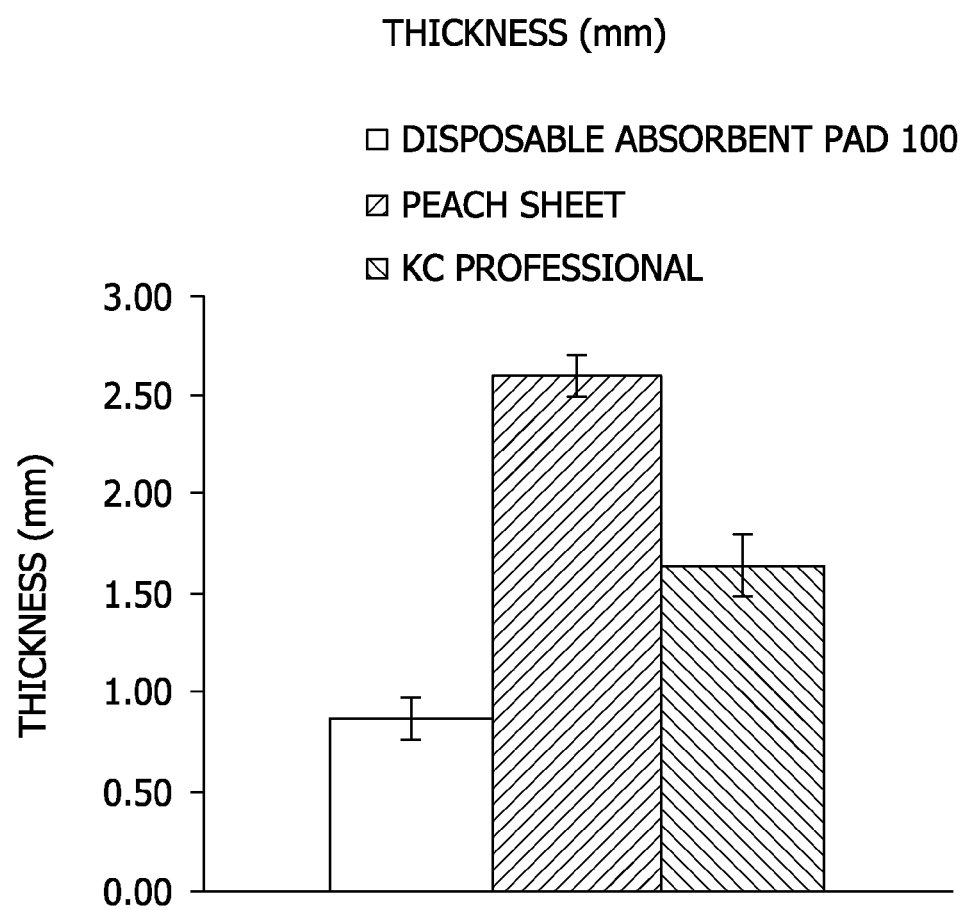
FIG. 12 is a graph depicting the results of a thickness test.

Data results that correspond to FIG. 12 and include the results from testing the thickness of each pad.

| Product Type | Specimen No. | Thickness (mm) |
|---|---|---|
| The Absorbent Pad Described Herein | 1 | 0.77 |
|  | 2 | 0.89 |
|  | 3 | 0.76 |
|  | 4 | 0.90 |
|  | 5 | 1.03 |
|  | Ave. | 0.87 |
|  | Std. | 0.11 |
| Tranquility Peach Sheet Pad | 1 | 2.45 |
|  | 2 | 2.55 |
|  | 3 | 2.67 |
|  | 4 | 2.71 |
|  | 5 | 2.58 |
|  | Ave. | 2.59 |
|  | Std. | 0.10 |
| Kimberly-Clark Professional Bed Pads | 1 | 1.88 |
|  | 2 | 1.66 |
|  | 3 | 1.50 |
|  | 4 | 1.53 |
|  | 5 | 1.62 |
|  | Ave. | 1.64 |
|  | Std. | 0.15 |

As illustrated in Table 5 and FIG. 12, the absorbent pad 100 has a thickness that ranges from 0.76 mm to 1.03 mm, with an average of 0.87 mm. Accordingly, the thickness of the absorbent pad 100 is substantially less than the thickness of the other bed pads.

Experiment 6

In this experiment, the ratio of the Gurley stiffness to thickness was calculated. More specifically, the results of the Gurley stiffness data that was measured in Experiment 4 was compared with the results of the thickness data that was measured in Experiment 5.

TABLE 6

Figure 13:
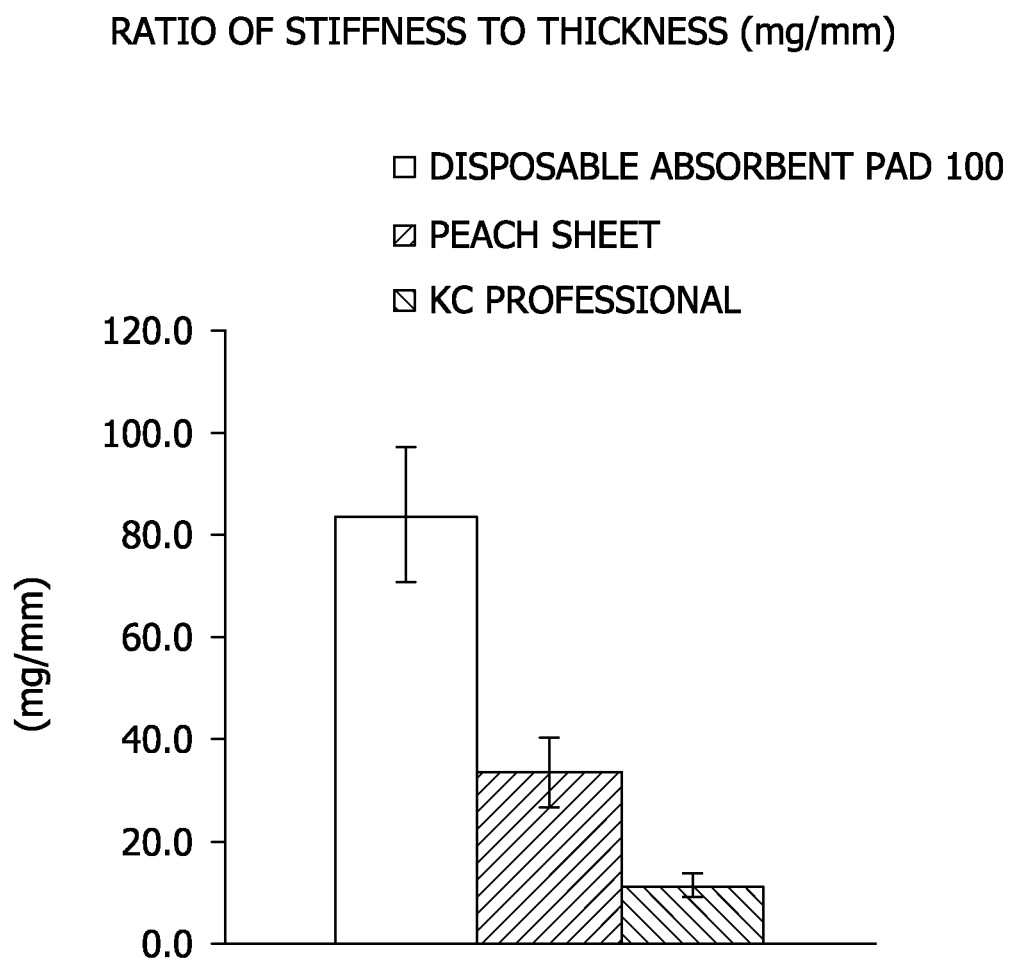
FIG. 13 is a graph depicting the results of a Gurley stiffness to thickness ratio test.

Data results that correspond to FIG. 13 and include the results from the calculation of the ratio of Gurley stiffness to thickness of each pad.

| Product Type | Specimen No. | Gurley Stiffness/Thickness (mg/mm) |
|---|---|---|
| The Absorbent Pad Described Herein | 1 | 93.9 |
| | 2 | 90.6 |
| | 3 | 91.4 |
| | 4 | 81.9 |
| | 5 | 62.1 |
| | Ave. | 84 |
| | Std. | 13.1 |
| Tranquility Peach Sheet Pad | 1 | 31.2 |
| | 2 | 28.9 |
| | 3 | 31.8 |
| | 4 | 45.6 |
| | 5 | 31.2 |
| | Ave. | 33.7 |
| | Std. | 6.7 |
| Kimberly-Clark Professional Bed Pads | 1 | 9.1 |
| | 2 | 14.7 |
| | 3 | 11.1 |
| | 4 | 13.8 |
| | 5 | 10.3 |
| | Ave. | 11.8 |
| | Std. | 2.4 |

As illustrated in Table 6 and in FIG. 13, the absorbent pad 100 has a Gurley stiffness to thickness ratio that ranges from 62.1 mg/mm to 93.9 mg/mm, with an average thickness ratio of 84 mg/mm. Accordingly, the Gurley stiffness to thickness ratio of the absorbent pad 100 is substantially greater than the other pads.

Experiment 7

In this experiment, five different pads for each of the absorbent pads 100, the Tranquility bed pads, and the Kimberly-Clark Professional bed pads were tested to determine the internal cohesion for each of the pads. More specifically, each of the pads were tested in the same manner as described for Experiment 3, except that the values did not need to be normalized based on adhesive size limitations. The standard cohesion test method was performed with a 2"×4" sample of a bed pad laminate. The sample was taken roughly from the center of each bed pad. The sample was then attached to the bottom of the tester by a piece of 2 sided tape. They were each then pressed together with 60 psi of pressure for 3 seconds. Another piece of 2 sided tape was then added to a 1"×1" square and it was attached to the top NW with 60 psi of pressure for 10 seconds. They were then pulled apart and a value was recorded based on how much force was required to release the layers of pad from one another

TABLE 7

Figure 14:
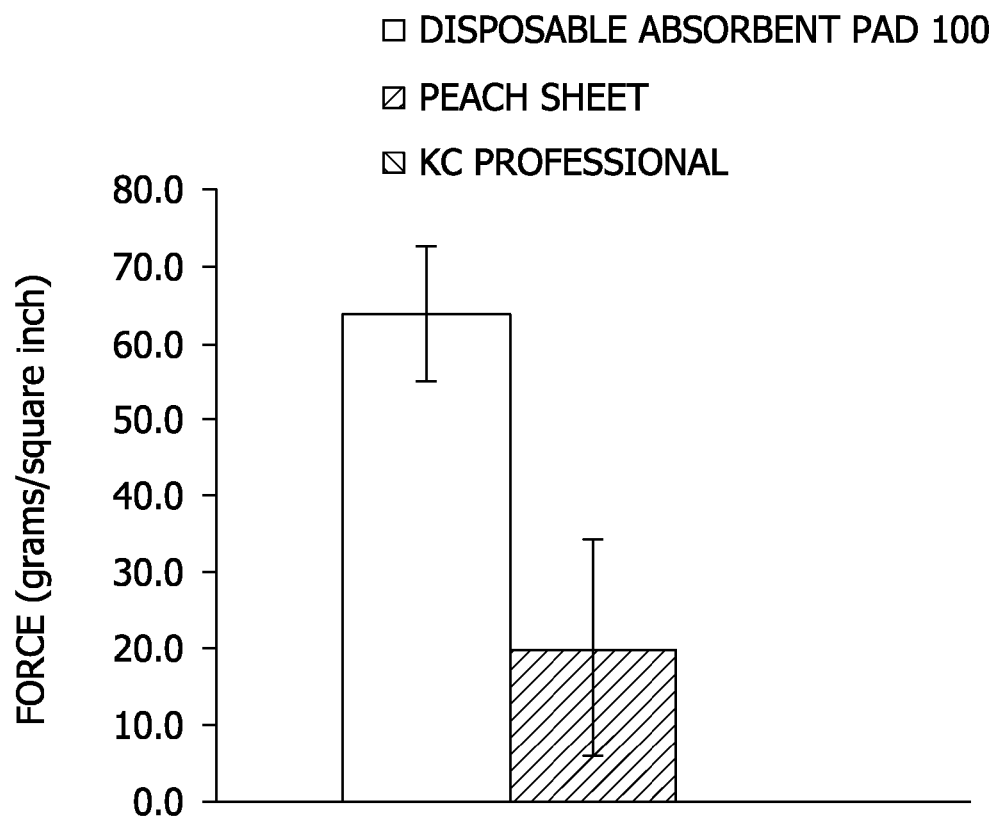
FIG. 14 is a graph depicting the results of an internal cohesive force experiment testing the cohesion between the absorbent structure and the top sheet and back sheet.

Data results that correspond to FIG. 14 and include the results from testing the internal cohesive force within each pad.

| Product Type | Specimen No. | Internal Cohesive Force (grams/sq. in.) |
|---|---|---|
| The Absorbent Pad Described Herein | 1 | 60 |
| | 2 | 80 |
| | 3 | 60 |
| | 4 | 60 |
| | 5 | 60 |
| | Ave. | 64 |
| | Std. | 8.9 |
| Tranquility Peach Sheet Pad | 1 | 20 |
| | 2 | 20 |
| | 3 | 0 |
| | 4 | 40 |
| | 5 | 20 |
| | Ave. | 20 |
| | Std. | 14 |
| Kimberly-Clark Professional Bed Pads | 1 | 0 |
| | 2 | 0 |
| | 3 | 0 |
| | 4 | 0 |
| | 5 | 0 |
| | Ave. | 0 |
| | Std. | 0 |

As illustrated in Table 7 and FIG. 14, the disposable absorbent pad 100 has a substantially higher internal cohesive force than the known bed pads. More specifically, the disposable absorbent pad 100 had an internal cohesive force ranging from 60 grams per square inch to 80 grams per square inch, with an average of 64 grams per square inch.

When introducing elements of the present invention or the preferred embodiment(s) thereof, the articles "a", "an", "the", and "said" are intended to mean that there are one or more of the elements. The terms "comprising," "including", and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. A disposable absorbent pad for engaging a substrate, the disposable absorbent pad comprising an absorbent structure configured to absorb fluid and a pressure sensitive adhesive applied to an underlying surface of the absorbent structure, the disposable absorbent pad being configured to lie generally planar when the pad is placed in engagement with the substrate and to provide a shear strength between the pad and the substrate when the pad is placed in engagement with the substrate between about 1,500 grams per square inch and about 3,500 grams per square inch.

2. The disposable absorbent pad of claim 1 wherein the pad is configured to provide a shear strength between the pad and the substrate when the pad is placed in engagement with the substrate between about 2000 grams per square inch and about 3000 grams per square inch.

3. The disposable absorbent pad of claim 2 wherein the pad is configured to provide a shear strength between the pad and the substrate when the pad is placed in engagement with the substrate between about 2200 grams per square inch and about 2500 grams per square inch.

4. The disposable absorbent pad of claim 1 wherein the pad is configured to provide a peel strength between the pad and the substrate when the pad is placed in engagement with the substrate between about 200 grams per inch and about 500 grams per inch.

5. The disposable absorbent pad of claim 4 wherein the pad is configured to provide a peel strength between the pad and the substrate when the pad is placed in engagement with the substrate between about 250 grams per inch and about 450 grams per inch.

6. The disposable absorbent pad of claim 5 wherein the pad is configured to provide a peel strength between the pad and the substrate when the pad is placed in engagement with the substrate between about 300 grams per inch and about 350 grams per inch.

7. The disposable absorbent pad of claim 1 wherein the adhesive provides the shear strength between the pad and the substrate.

8. The disposable absorbent pad of claim 7 further comprising a back sheet having a first surface and a second surface, the adhesive being applied to the second surface of the back sheet, the absorbent structure being attached to the first surface of the back sheet.

9. The disposable absorbent pad of claim 8 further comprising a top sheet, the absorbent structure being disposed between the top sheet and the back sheet.

10. A package comprising at least one disposable absorbent pad of claim 1.

11. A disposable absorbent pad for adhering to a substrate, the disposable absorbent pad comprising a top sheet, a back sheet and an absorbent structure configured to absorb fluid, the back sheet having a first surface and a second surface, the absorbent structure being disposed between the top sheet and the back sheet, the absorbent structure being attached to at least one of the top sheet and the back sheet, the attachment between the absorbent structure and the at least one of the top sheet and back sheet having an internal cohesive force between about 45 grams per square inch and about 100 grams per square inch, the second surface of the back sheet having adhesive applied thereto for adhering the pad to a substrate, the adhesive covering between about 5 percent and about 100 percent of the second surface, the disposable absorbent pad being configured to provide a shear strength between the pad and the substrate when the pad is placed in engagement with the substrate between about 1,500 grams per square inch and about 3,500 grams per square inch.

12. The disposable absorbent pad of claim 11 wherein the attachment between the absorbent structure and the at least one of the top sheet and back sheet has an internal cohesive force between about 55 grams per square inch and about 80 grams per square inch.

13. The disposable absorbent pad of claim 12 wherein the attachment between the absorbent structure and the at least one of the top sheet and back sheet has an internal cohesive force of about 64 grams per square inch.

14. The disposable absorbent pad of claim 11 wherein the absorbent structure is adhered to both the top sheet and the back sheet.

15. The disposable absorbent pad of claim 11 wherein the absorbent structure is pattern bonded.

16. The disposable absorbent pad of claim 15 wherein the pattern bonds of the absorbent structure comprise point bonds.

17. The disposable absorbent pad of claim 15 wherein the back sheet is free from point bonds.

18. The disposable absorbent pad of claim 11 wherein the disposable absorbent pad has a thickness less than about 1.5 millimeters.

19. The disposable absorbent pad of claim 18 wherein the disposable absorbent pad has a ratio of Gurley stiffness to thickness between about 40 mg/mm and about 100 mg/mm.

20. A package comprising at least one disposable absorbent pad set forth in claim 11.

21. A disposable absorbent pad for adhering to a substrate, the disposable absorbent pad comprising:
an absorbent structure configured to absorb fluid;
a back sheet having a first surface and a second surface, the second surface of the back sheet having adhesive applied thereto for adhering the pad to a substrate,
wherein the disposable absorbent pad is sized and shaped for placement on a bed and having a generally rectangular shape with a length between about 12 inches and about 84 inches and a width between about 12 inches and about 72 inches, the adhesive covering between about 10 percent and about 60 percent of the second surface, the absorbent structure being attached to the back sheet, the attachment between the absorbent structure and the back sheet having an internal cohesive force between about 45 grams per square inch and about 100 grams per square inch, the disposable absorbent pad being configured to provide a shear strength between the pad and the substrate when the pad is placed in engagement with the substrate between about 1,500 grams per square inch and about 3,500 grams per square inch.

22. The disposable absorbent pad of claim 21 wherein the adhesive covers between about 10 percent and about 40 percent of the second surface.

23. The disposable absorbent pad of claim 22 wherein the adhesive covers about 16 percent of the second surface of the back sheet.

24. The disposable absorbent pad of claim 21 wherein the adhesive is applied to the second surface of the back sheet in a plurality of discrete areas.

25. The disposable absorbent pad of claim 21 wherein the back sheet is generally rectangular and includes four corners, each of the four corners of the generally rectangular back sheet having a discrete area of adhesive applied adjacent thereto.

26. The disposable absorbent pad of claim 25 wherein each of the discrete areas of adhesive is covered by a peel strip.

27. A package comprising at least one disposable absorbent pad of claim 21.

* * * * *